(12) United States Patent
Speidel et al.

(10) Patent No.: US 11,399,791 B2
(45) Date of Patent: Aug. 2, 2022

(54) SYSTEM AND METHOD FOR FLOW-RESOLVED THREE-DIMENSIONAL IMAGING

(71) Applicant: Wisconsin Alumni Research Foundation, Madison, WI (US)

(72) Inventors: Michael Speidel, Madison, WI (US); Erick Oberstar, Verona, WI (US); Martin Wagner, Madison, WI (US); Mariya Pravdivtseva, Lubeck (DE)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 75 days.

(21) Appl. No.: 16/837,801

(22) Filed: Apr. 1, 2020

(65) Prior Publication Data

US 2021/0307712 A1 Oct. 7, 2021

(51) Int. Cl.
| | |
|---|---|
| *G06K 9/00* | (2022.01) |
| *A61B 6/00* | (2006.01) |
| *G06T 7/20* | (2017.01) |
| *G06T 5/50* | (2006.01) |

(52) U.S. Cl.
CPC .............. *A61B 6/504* (2013.01); *G06T 5/50* (2013.01); *G06T 7/20* (2013.01); *G06T 2207/10081* (2013.01); *G06T 2207/20224* (2013.01); *G06T 2207/30101* (2013.01)

(58) Field of Classification Search
CPC .................................................... A61B 6/504
See application file for complete search history.

(56) References Cited

U.S. PATENT DOCUMENTS

| | | | | |
|---|---|---|---|---|
| 2012/0307964 | A1* | 12/2012 | Hall | A61B 6/03 378/8 |
| 2012/0321156 | A1* | 12/2012 | Waechter-Stehle | G06T 7/254 382/130 |
| 2015/0025370 | A1* | 1/2015 | Neukirchen | A61B 6/504 600/432 |
| 2015/0379706 | A1* | 12/2015 | Leonhardt | G06T 7/0012 382/131 |
| 2016/0135775 | A1* | 5/2016 | Mistretta | G06T 7/0012 600/419 |
| 2017/0039734 | A1* | 2/2017 | Langan | A61B 6/025 |
| 2019/0357778 | A1* | 11/2019 | Wilson | A61B 5/0275 |
| 2020/0022664 | A1* | 1/2020 | Moore | G06T 7/0016 |

* cited by examiner

*Primary Examiner* — Oneal R Mistry
(74) *Attorney, Agent, or Firm* — Quarles & Brady, LLP

(57) ABSTRACT

A system and method is provided for imaging a contrast agent. The system includes a power injector that delivers a contrast agent as a series of boluses using a known period, flow rate, or duration and with a rate of at least one or more separate boluses per cardiac cycle. An x-ray imaging system acquires a reference dataset of the subject before the contrast agent is delivered and acquires an imaging dataset as the series of boluses are delivered to the subject, wherein multiple images are acquired of the subject per bolus. A computer system receives the reference dataset and the imaging dataset from the x-ray imaging system and reconstructs the reference dataset and the imaging dataset using a reconstruction process that removes the subject from the images to generate time-resolved volumetric images of the contrast agent moving within a volume of the subject without the subject.

37 Claims, 6 Drawing Sheets

SYSTEM AND METHOD FOR FLOW-RESOLVED THREE-DIMENSIONAL IMAGING

STATEMENT REGARDING FEDERALLY SPONSORED RESEARCH

This invention was made with government support under 5R01HL116567 awarded by the National Institutes of Health. The government has certain rights in the invention.

BACKGROUND

The present disclosure relates to systems and methods for medical image data acquisition and/or reconstruction. More particularly, systems and method are provided for producing medical images that can be flow-resolved and three-dimensional.

Clinical outcomes for many conditions are directly correlated to the amount of accurate information that is available to a clinician and the speed with which the information or updated information can be provided. The ability to successfully diagnose and treat vascular conditions, such as aneurysms, is highly dependent upon detailed and accurate information being available to clinicians. Furthermore, the dependence upon and availability of accurate information extends well beyond the diagnostic and treatment phase.

As but one example, aneurysm intervention is often designed to induce changes in flow pattern via interventional device deployment. However, current methods of imaging the effects of the device on flow patterns in the interventional suite are inadequate. That is, patient-specific intra-procedural evaluation of flow pattern changes is hindered by a lack of suitable imaging methods. Conventional 2D projection x-ray imaging, generally two-dimensional (2D) digital subtraction angiography (DSA) uses an injected contrast agent to visualize the flow of blood and can be performed in the interventional suite. However, the 2D DSA image does not provide a complete picture of the complex three-dimensional (3D) flow patterns that exist inside large vascular structures, such as an aneurysm sac. Although the recently developed time-resolved or "4D" DSA technology can be coupled with separate flow information to provide time-resolved imaging of contrast agent flow through a 3D vascular tree, it does not portray flow dynamics that are internal to a specific vascular structure. That is, flow-resolved 4D DSA does not show the three-dimensional dynamics, including eddying or the like, within an aneurysm sac.

Other techniques, such as 4D-flow MRI have substantial shortcomings due to the fact that the underlying imaging modality is generally incompatible with the interventional suite. That is, to perform a 4D-flow MRI study, the patient must be removed from the interventional suite. As such, even if the 4D-flow MRI study reveals that further corrective efforts would be required or are desirable, an intervention must be performed. That is, 4D-flow MRI can provide a detailed image of complex blood flow patterns even into an aneurysm or the like, but it is not compatible with an interventional environment that requires full patient access, rapid imaging, and a variety of catheter devices that may contain metal. Furthermore, many 4D-flow MRI implementations require the use of a different contrast agent, gadolinium, from the contrast agent used with the x-ray imaging performed in many interventional suites and some patients, such as those with limited kidney functions are contra-indicated for use with such MRI contrast agents.

With this in mind, some have proposed to forgo actual patient data and simply rely on computational fluid dynamics (CFD) simulations to evaluate interventions. Even beyond the potential for modeling inaccuracies, in practice this is not practical in the interventional setting because it requires lengthy computations and the accuracy is sensitive to boundary conditions that may be unknown or poorly characterized.

Therefore, it would be desirable to have systems and methods for producing 3D images of internal flow patterns that are compatible with an interventional setting to provide clinicians with new and valuable information that can guide the intervention.

SUMMARY

The present disclosure overcomes the aforementioned drawbacks by providing systems and methods that utilize a series of contrast boluses and reconstruct images that treat the contrast boluses as the "object" being imaged. By coordinating the boluses using a power injector, the imaging acquisition, and the reconstruction of the acquired data, 3D volumes of the flow dynamics of the subject, even flow dynamics within an irregular or non-tubular vascular structure, such as an aneurysm, can be created.

In accordance with one aspect of the present disclosure, a system is provided for acquiring images of three-dimensional flow within an interior volume of a subject. The system includes a power injector programmable to deliver a contrast agent as a series of boluses using a known at least one of period, flow rate, or duration and with a rate of at least one or more boluses per cardiac cycle of the subject. The system also includes an x-ray imaging system configured to acquire a reference dataset of the subject before the contrast agent is delivered to the subject and to acquire an imaging dataset as the series of boluses are delivered to the subject, wherein multiple images are acquired of the subject per bolus. A computer system is provided that is configured to receive the reference dataset and the imaging dataset from the x-ray imaging system reconstruct the reference dataset and the imaging dataset using a reconstruction process that removes the subject from the images to generate time-resolved volumetric images of the contrast agent moving within a volume of the subject without the subject.

In accordance with another aspect of the present disclosure, a method is provided for creating an image of flow within a subject. The method including programming a power injector to deliver a contrast agent to the subject as a series of boluses to deliver one or more boluses per cardiac cycle using a known at least one of period, flow rate, or duration of the series of boluses. The method also includes acquiring a reference image dataset of the subject in the absence of the contrast agent and acquiring a medical image dataset of the subject during operation of the power injector as the one or more boluses per cardiac cycle are delivered to the subject, wherein multiple images are acquired per bolus. The method further includes reconstructing the medical image dataset and the reference image dataset to create a series three-dimensional (3D) volumes of the contrast agent as the contrast agent dynamically moves with the known at least one of period, flow rate, or duration through the subject.

The foregoing and other aspects and advantages of the invention will appear from the following description. In the description, reference is made to the accompanying drawings which form a part hereof, and in which there is shown by way of illustration a preferred embodiment of the inven-

DETAILED DESCRIPTION

Figure 1A:
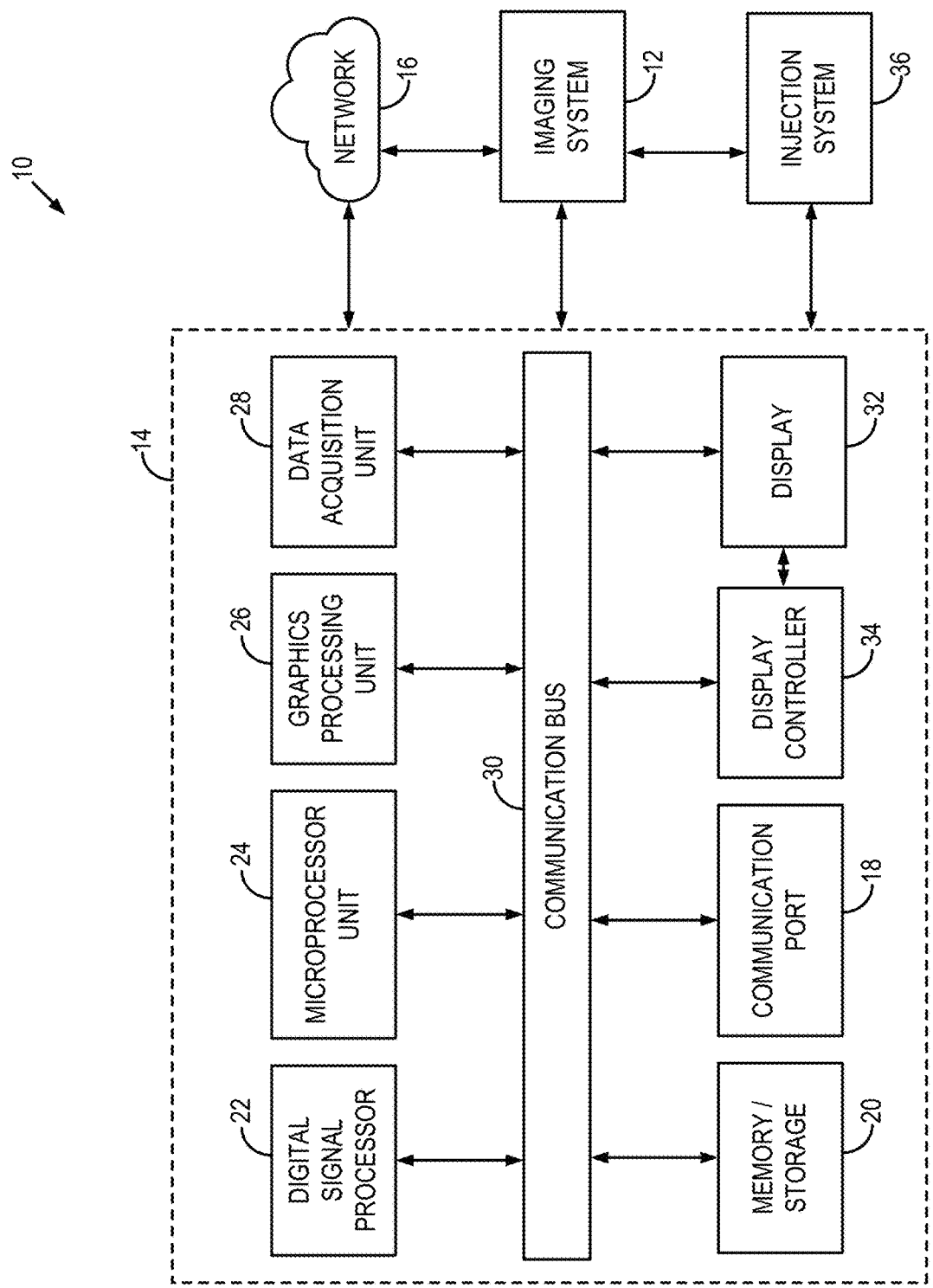
FIG. 1A is a schematic diagram of an example computer system in accordance with the present disclosure and that can be configured to implement the methods described herein.

Referring now to FIG. 1A, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26 (or other processors, such as field programmable gate arrays (FPGAs)). If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or hardwire used for switching data between the peripherals or between any components, such as the communication buses described above.

The computer system 14 may also include or be connected to a display 32. To this end, the computer system 14 may include a display controller 34. The display 32 may be a monitor connected to the computer system 14 or maybe integrated with the computer system 14, such as in portable computers or mobile devices.

As will be described, an injection system 36 may also be included that can be used within the system 10 to carry out a method for flow-resolved 3D angiography. To this end, the imaging system 12 may be an x-ray imaging system configured to acquire an x-ray angiogram. This may be achieved using a variety of imaging constructs. For example, a rotation x-ray angiogram may be acquired. Also, a rotational digital subtraction angiogram may be acquired. Further still, a limited-angle rotational acquisition, or tomosynthesis-style gated acquisition, may be performed. In any case, as will be described, during acquisition of image data, short, low-volume boluses of radiographic contrast agent can be periodically injected into the vascular structure via the injection system 36 to acquire images showing flow dynamics that function as the "object" of the imaging study.

Figure 1B:
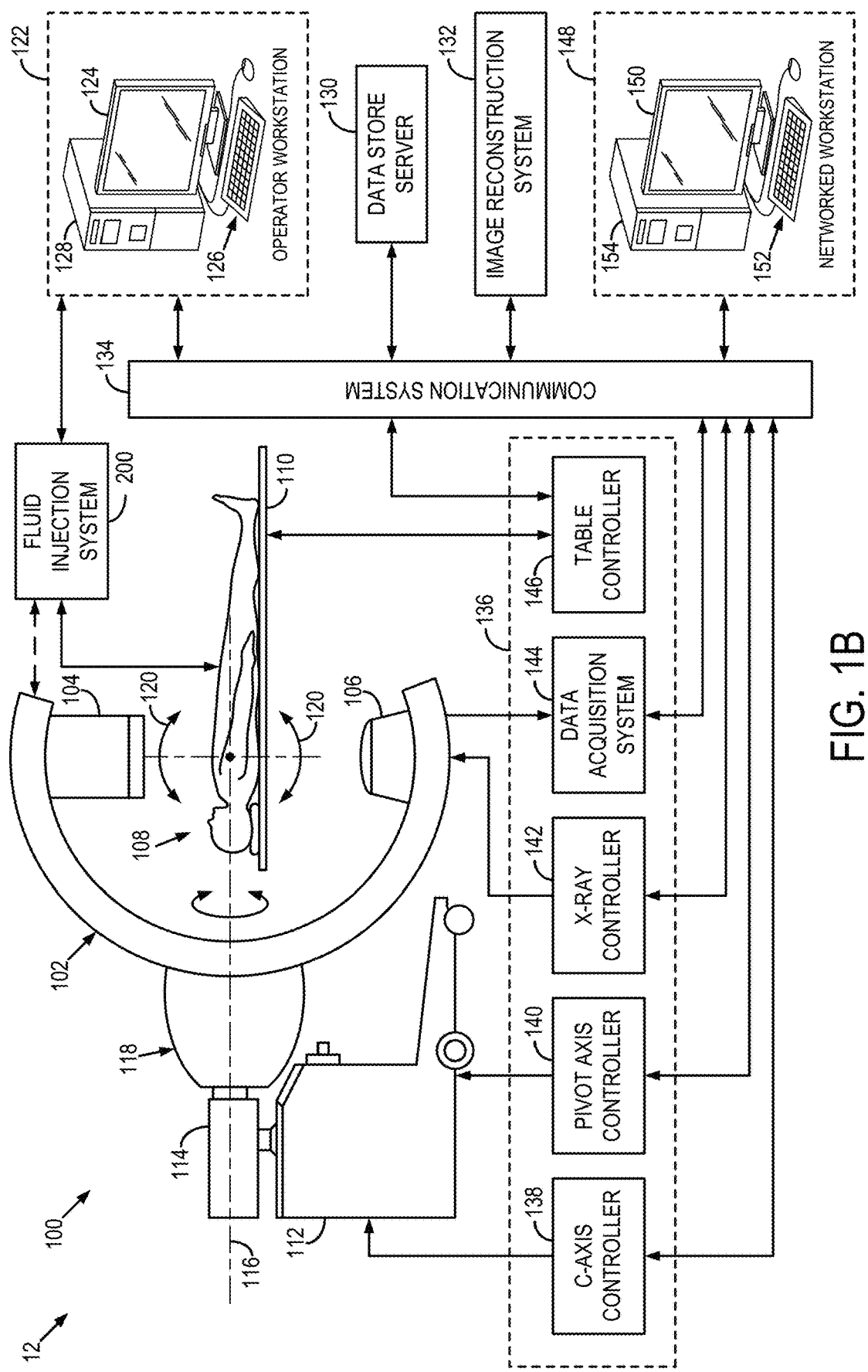
FIG. 1B is a schematic diagram of a C-arm x-ray computed tomography (CT) imaging system configured in accordance with the present disclosure.

Referring to FIG. 1B, one, non-limiting example of the imaging system 12 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems. However, systems and methods described herein may be used with any of a variety of systems that facilitate interventional procedures, and may also be used with CT, MRI, or other systems that are not designed for interventional or image-guided procedures.

Referring again to FIG. 1B, the open or interventional x-ray imaging system 100 includes a gantry 102, in this non-limiting example, having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a beam, fan-beam, or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a drive assembly 118 on its outer end. The gantry 102 is fastened to the drive assembly 118 and is coupled to a drive motor (not shown) that slides the gantry 102 to revolve it about a C-axis, as indicated by arrows 120. The pivot axis 116 and C-axis are orthogonal and intersect each other at the isocenter of the x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles.

As will be described, the overall x-ray imaging system may include a fluid injection system 200. The fluid injection system 200 may deliver a fluid, such as a contrast agent, to the subject during the imaging acquisition. As will be described, the delivery of the contrast agent may be configured such that each short bolus of contrast agent provides a compact measurable x-ray signal that is carried through the anatomic structure by blood flow.

The x-ray imaging system 100 also includes an operator workstation 122, which typically includes a display 124, one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store server 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Figure 2:
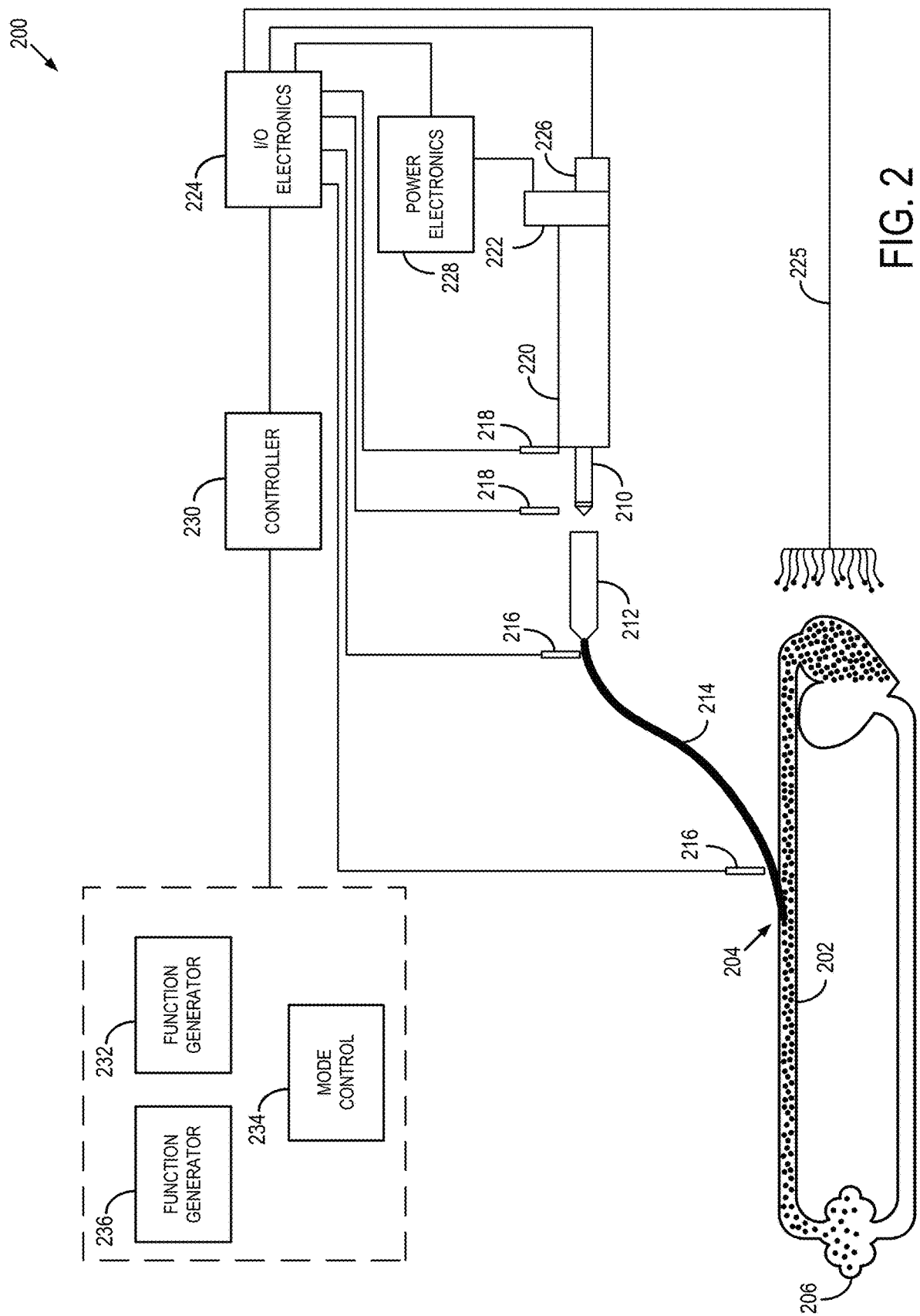
FIG. 2 is a block diagram for a power injection system that may be used in accordance with the present disclosure.

Referring now to FIG. 2, the fluid injection system 200 may include injection components that include plungers 210, a syringe barrel(s) 212, and a catheter 214, shown introduced into a vascular structure 202, which may be an artery or vein 202 by way of example, at an injection site 204. That is, a system, whether including a syringe or any other injection mechanism is provided to deliver contrast density variations that can be achieved at constant flow rate of dynamically mixed saline and contrast, or modulation of contrast flow rate. Modulated fluid concentration injected therein is utilized to assess characteristics of the vascular system including the artery (or vein) 202, such as at a downstream capillary bed 206 that may exhibit low pulsatile flow. Pressure transducers 216 may be utilized to monitor pressure at the points shown in the catheter 214, and a force transducer 219 may be used to detect forces at the end of the plunger.

Actuator componentry may include an actuator 220 such as a ball/screw lead driven by a gearbox and motor 222, which may be controlled via signals received at input/output (I/O) electronics 224, with feedback provided by an encoder 226. Though the encoder 226 is one option for implementation, other systems can also be used to accurately control velocity. Pump or motor control dynamics can also be monitored and used to control and derive or track velocity. Other inputs to the I/O electronics 224 may include an ECG leads 225, which provide an ECG signal that may be used, for example, to synchronize the modulation to the cardiac cycle. Power electronics 228 may further interact between the I/O electronics 224 and the gear box/motor 222. Further, limit switches 218 may be used to detect positions of plungers in the syringe barrel(s)

A computer controller 230 (including computing circuitry) operates using a function generator 232 to generate a user-selected function by which injected agent is to be modulated. The computer controller 230 may also operate using a mode controller 234, such as to control a type of injection and related operation. The computer controller 230 may also similarly control a further function generator 236 (e.g., where two different functions are used to control different circuit components). In this context, the computer controller 230 along with the I/O electronics 224, encoder 226 and power electronics 228 may operate in the electrical domain, with the function and mode components 232, 234, and 236 operating therewith. For instance, the function generator 232 may be implemented to generate a sine wave or square wave with a modulated frequency, which is used by the computer controller 230 to generate an output that controls actuation of the plunger(s) 210 for injecting a fluid at a variable sinusoidal rate or according to a gated square wave.

In some implementations, the fluid injection system 200 operates as follows. A syringe 212 filled with a contrast agent, such as a fixed iodine concentration can be modulated or a fixed flow rate of fixed concentration iodine can be modulated by the additional injection of a modulated diluting agent, such as saline. A user interface coupled via computer controller 230 that may facilitate the implementation of constant, sinusoidal, swept sine, white noise, square wave/duty cycle and simulated cardiac flow waveforms with user defined amplitudes, frequencies, and delays. Further, a window function such as Boxcar, Hamming, or Hanning may be applied to the waveform to help shape frequency domain characteristics. As but one non-limiting example, the actuators used in this context may generate forces that, when applied to a 40 mm diameter 150 mL syringe, flows in a clinically valuable range, such as 0 to 50 mL/s out of each syringe.

Thus, the fluid injection system 200 may operate as a power injection apparatus introducing temporal variations in flow rate and/or concentration of a contrast agent. This approach may be used to maintain stronger contrast pulsatility in the distal portions of a vascular network, thereby enabling flow quantification in distal vessels. When mixed with fluid prior to injection, the concentration of the contrast agent can be varied by increasing or decreasing its flow rate, and/or by increasing or decreasing the flow rate of fluid with which the contrast agent is mixed. These approaches facilitate varying the rate of injection over time according to a variety of modulation schemes, as may include sinusoidal, square, triangle, swept sine, white noise, aperiodic, or other user-programmable profiles. Accordingly, specific and different periods of oscillation, peak and mean amplitudes, phase, and frequency can be utilized with dynamic modulation. For instance, contrast agent injection may be purposefully modulated at a frequency lower than the cardiac rate in order to improve contrast pulsatility in distal vasculature and enable more reliable DSA-based flow quantification. Further, one or more of these modulation schemes may be implemented with a bias, for example where flow rate is varied between high and low values around a bias level of flow rate, where the low value may even be a zero, or as small positive value.

As utilized herein, the term dynamically modulating refers to modulation that is dynamically changed during the application of the modulation. For example, a flow rate of agent may be modulated between respective values at a particular frequency. Dynamically modulating such a flow rate of agent involves changing the frequency at which the flow rate is modulated, such as by implementing a frequency sweep, during the modulation. Accordingly, dynamic modulation does not refer to a modulation that is static, such as by maintaining a frequency at which modulation is implemented.

In some implementations, a dual-barrel power injector may be used to respectively inject agent and other fluid such as saline via each of the barrels, with the two being mixed prior to and/or during injection. The dual-barrel power injector may include plunger actuators or other fluid delivery components (e.g., gears, pumps) that are independently controlled. For general information regarding injecting agents, and for specific information regarding mechanisms for injection that may be utilized in connection with one or more embodiments, a syringeless injector may be implemented such as the CT Exprès in jector, available from Bracco Imaging SpA—Bracco Imaging Italia srl, Via Caduti di Marcinelle, 13 20134—Milano. As such, both concentration vs. time and total flow vs. time can be modulated. By controlling the injector barrels independently, specific and different periods of oscillation, peak and mean amplitudes can be defined. In this context, the injector barrels may be controlled together in a manner similar to single barrel injectors relative to pressures and other conditions that facilitate safe use with humans.

Consistent with the above, certain embodiments involve characterizing a cardiovascular system using force and/or pressure measurements. For instance, backpressure may be measured upstream from an injection site, as may be caused by injecting into a blood vessel with cardiac flow. Such backpressure may induce back force of 0.037 lbf per mmHg of pressure for a fluid system. This corresponds with a ~0.19 lbf force for a 5 mmHg change in pressure. For lower concentrations of a contrast agent such as Iohexol (or contrast with similar viscosity), 12-bit (or higher) force resolutions can be used to measure pressure changes on the order of 5 mmHg (or better), facilitating intra-arterial pressure measurements from an injector itself. Higher resolution than 12 bit may be utilized for higher viscosity contrast agents.

In some configurations, disturbance forces can be detected as an acceleration to motion control, noting that Force=Mass*Acceleration. This acceleration alters the velocity trajectory as an acceleration disturbance into the system that can be detected by velocity measurement with an appropriately sampled high-resolution encoder (e.g., higher than 5000 lines per revolution quadrature decoded [20,000 increments per revolution]).

In other configurations, pressure can be monitored with pressure transducers in line with a fluid system at the outlet of a syringe or the outlet of a tube into a catheter. Both locations facilitate measurement points of the disturbance pressure from the cardiovascular system. Pressure sensitivity may be set to suit particular embodiments. For instance, where approximately 85% of the pressure drop is across the catheter, a pressure sensitivity 1 mmHg over the range of system pressures utilizes a 14-bit or higher resolution on a pressure transducer at the tube/catheter interface.

Various aspects of the present disclosure are directed to a method in which a flow rate of agent being injected into a vascular system (e.g., along with saline) is dynamically modulating over a range of flow rates, and the vascular system is characterized based on its response to the dynamic modulation. Modulating the flow rate of the agent may involve one or more of a variety of types of modulation, which may result in a different concentration of the agent being injected, a different amount of the agent being injected and/or a different amount of overall liquid including the agent being injected. In some implementations, the concentration of the agent mixed with a constant flow of other fluid such as saline is modulated. In other implementations, the concentration of the agent in liquid can be maintained while modulating the total volume of the liquid. In yet other implementations, the actual flow rate of the agent can be unchanged while the relative flow rate of the agent to the liquid in which it is injected is modified by modifying the actual flow rate of the liquid.

Consistent with the above-noted discussion, it has been recognized/discovered that utilizing dynamic modulation, such as by applying low frequency modulation of injected agent flow rate or concentration, enhances the ability to detect related changes in the agent at such distal locations. In many contexts, this approach imparts data such as a signature to volumes of vascular fluid at an injection site, which can then be recognized at distal locations.

In various contexts, the remote or distal area at which the vascular system is characterized may be either upstream or downstream relative to the injection site. For instance, in applications such as imaging flow dynamics in an aneurysm, the systems and methods described herein can provide detailed information regarding flow or flow changes within or surrounding the aneurysm. In the clinical application of embolization of vasculature in the liver, reflux of contrast agent may be used to determine when the procedure is complete. The reflux may involve a periodic upstream flow.

As described herein, a "bolus" or multiple "boluses" are delivered. The formation of a given bolus or a collection of boluses can be achieved using any of a variety of techniques that modulate the amount of contrast agent delivered at any given time. Thus, a "bolus" or a series of "boluses" are a reflected by a modulation of contrast delivery between a high amount of contrast and a low amount of contrast. The "high" amount may be achieved via changes in the volume of contrast delivered, the concentration of the contrast delivered, or other techniques for achieving a "high" or "higher" amount of contrast compared to another "low" or "lower" amount. The "low" or "lower" amount can be zero contrast, or may be an amount of contrast that is just lower than the "high" or "higher" amount. Thus, deliver of a bolus or series of boluses can be achieved by the dynamic modulation of the contrast agent, such as achieved by using the above-described fluid injection system 200.

The dynamic modulation can be carried out using a variety of approaches, to suit particular applications. For instance, volume of agent delivered may be varied. Also, one or more of flow rate of the agent, concentration of the agent, and flow rate of the liquid may be modulated. Such modulation may include modulating between high and low values respectively above and below an offset value, such that a low rate still involves a positive rate (e.g., so as not to encompass an effective a negative flow or concentration). The modulation may involve pseudo-periodic, periodic, aperiodic or arbitrary modulation, or may involve bolus shaping. Various functions may be implemented for the modulation, such as by using a waveform including one or more of a sinusoidal waveform, a swept sinusoidal waveform, a triangle waveform, a square waveform, an arbitrary waveform, and a combination thereof. Frequency may be modulated (e.g., using a frequency sweep), amplitude (e.g., concentration or volume) may be modulated, or a phase of a waveform may be shifted. Higher order modulation schemes may also be utilized, such as those involving the modulation of multiple frequency waveforms together.

In some configurations, the flow rate of the agent is modulated using cardiovascular flow of blood in the vascular system to modulate the concentration of the agent flowing through the system. Changes in the concentration of the agent are detected at a remote portion of the cardiovascular system, relative to a portion of the vascular system at which the liquid is injected.

In one non-limiting example, cardiovascular flow of blood in the vascular system is used as a carrier signal, and data is coded onto the cardiovascular flow by modulating a frequency, phase or amplitude characteristic of the concentration of the agent injected via the liquid. For instance, amplitude may be varied between maximum and minimum flow rates, with the minimum being at or above zero. The vascular system is then characterized by detecting changes in the data coded onto the cardiovascular flow as the blood flows through the vascular system.

Another configuration is directed to an ECG gating approach. In this context, the flow rate (e.g., volume and/or concentration) of agent in the liquid can be modulated for generating contrast flows of the agent that are synchronized with the cardiac cycle of the vascular system. For instance, the modulation may synchronize to a systolic or diastolic period of the cardiac cycle. As such, ECG gating can be effected, in which a phase relationship of modulation of the agent is synchronized with the cardiac cycle.

A particular use-case scenario involves utilizing short duration contrast pulsation for imaging aneurysms, in which stream lines and jets inside and entering into the aneurysm may be monitored as well. For instance, low duty cycle square waves can be utilized for the modulation at a specific frequency, such as will be described.

Figure 3A:
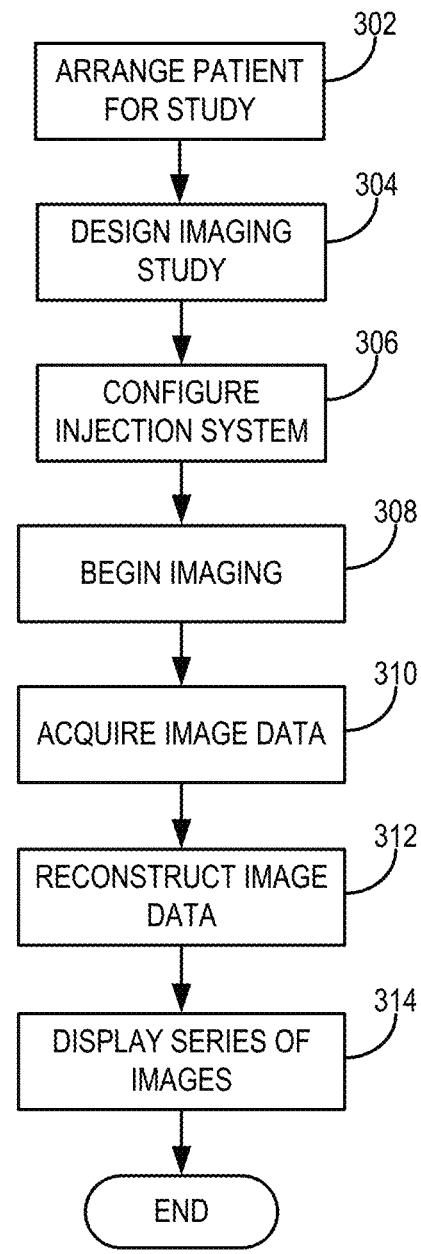
FIG. 3A is a flow chart setting forth some examples of steps in an imaging process in accordance with the present disclosure.

Specifically, referring now to FIG. 3A, a flow chart is provided setting forth steps of a process for flow-resolved 3D x-ray angiography in accordance with the present disclosure. The process beings at process block 302 with arranging the patient for the study. For example, this may include positioning the patient for imaging with a system such as described above with respect to FIGS. 1A and 1B to acquire a rotational x-ray angiogram, rotational digital subtraction angiogram, a limited-angle rotation dataset, or tomosynthesis-style gated dataset, or other imaging dataset. This may also include determining parameters about the patient, such as heart rate or the like, and may entail configuring monitoring systems on the patient, such as ECG leads 225 of FIG. 2. In this way, one can prospective gate the injection and retrospectively gate of the reconstruction.

Then, at process block 304, an imaging study is designed and/or imaging parameters are selected. As will be described, coordination of the operation of contrast injection with the performance of the imaging study, or vice versa or both, yields flow information not available previously. Specifically, at process block 306, a contrast agent injection system, such as described with respect to FIG. 2, is configured to periodically administer a series of specially-calibrated boluses or pulses of contrast agent to the subject. Notably, the boluses or pulses of contrast agent need not form square waves but are designed to vary between a "high" and "low," even if the "low" is not zero. Short, low-volume boluses of contrast agent are provided as a compact, measurable x-ray signal that is carried through the anatomic structure by blood flow to a target of the imaging study, such as an aneurysm.

More particularly, the duration, period, and/or rate of injection can be selected or coordinated with the projection imaging so that multiple images are acquired per injection period. In one non-limiting consideration, the rotation time of the gantry of the imaging system is selected and/or the injection timing is configured such that multiple injection cycles occur in the course of imaging. In one non-limiting example, to achieve a series of compact boluses, the injection period is selected to be approximately equal to, or a multiple of, the cardiac cycle. As another non-limiting example, a series of compact boluses achieved by selecting an injection period that is a subset of the cardiac cycle, such as every other beat in the cardiac cycle. In this way, the delivery of the boluses may be prospectively gated relative to the cardiac cycle. However, prospective gating may also be performed relative to other cycles, such as the repertory cycle, or the delivery of the boluses may not be gated relative to any physiological cycle. Finally, the contrast medium injection rate during a bolus and contrast medium volume per bolus is selected or adjusted to achieve a balance between image signal size, bolus deliver, and any desired integrity of native blood flow dynamics.

As disclosed herein, the present disclosure recognizes that careful coordination of a contrast cycle relative to a cardiac cycle of the patient and the imaging parameters can yield a set of projection images where i) the passage of a contrast bolus through the vascular structure has been imaged at multiple states within the injection cycle, and furthermore, ii) each state of contrast bolus passage (i.e., specific position and dispersion of contrast agent inside the vascular structure) has been imaged at multiple view angles.

In one non-limiting example, a frame rate of 15-30 frame/s may be selected at process block 304 and an injection period of 1 second selected at process block 306. At process block 308, x-ray projection images are acquired at a high rate as the x-ray system rotates around the subject as the injection process begins according to the coordinated plan. In the case of rotational acquisitions, one rotation or multiple rotations may be performed per injection. Imaging at process block 308 may begin with acquiring mask images before injection followed by continued imaging during execution of the coordinated plan. For example, with a 6-12 second rotation duration, this can allow for 6-12 injection cycles using a 1 second injection period.

Figure 4:
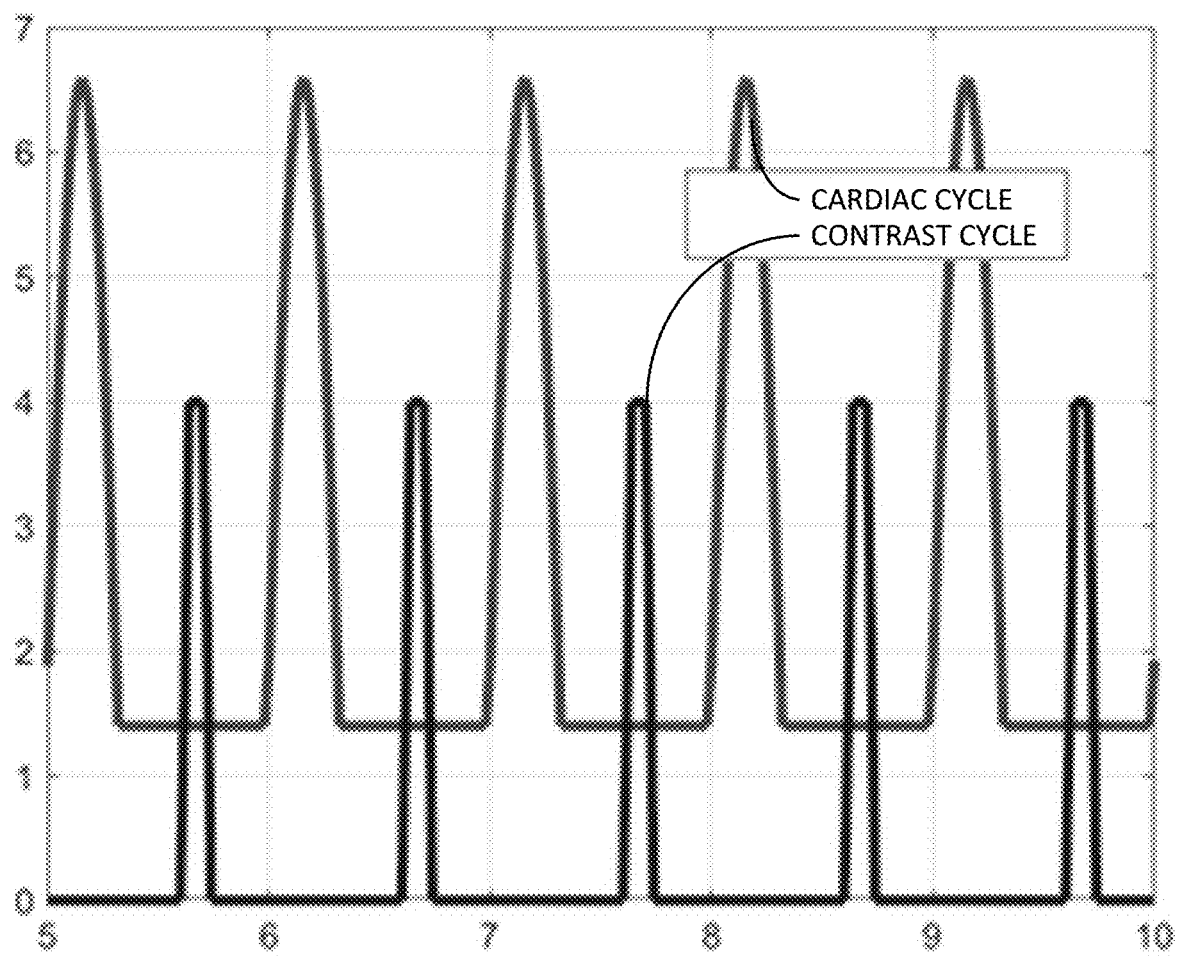
FIG. 4 is a graph of contrast and cardiac cycle in accordance with the present disclosure.

One such example of a coordinated injection and acquisition protocol is illustrated in FIG. 4. In this non-limiting example, the contrast injector programming was created for a subject with a 60 bpm heart rate. A square wave pulse train was used with 10% duty cycle and 1 Hz frequency. The contrast pulses were interlaced with the pulsatile cardiac flow. In the illustrated example, the contrast pulses were aligned halfway between systolic pulses of the cardiac cycle. As described, this configuration can be particularly advantageous for particular clinical applications. The flow rate was 4 mL/s during a square pulse and 0 mL/s between pulses. A total of 20 pulses were generated, and approximately 9 to 10 of these pulses occurred during the x-ray imaging acquisition. Each pulse injected approximately 0.4 mL of contrast agent. Therefore, the total required contrast volume for 9-10 pulses was approximately 4 mL.

With the patient parameters such as heart rate or cardiac cycle known, the imaging parameters set, and a coordinated injection protocol configured, image data can be acquired at process block 310, which includes performing the imaging study set at process block 304 and the injection protocol set at process block 306. In particular, to perform an angiographic study, two image datasets may be acquired. The first set is a "mask" or "non-contrast" image dataset. The second is a "fill" or "contrast-enhanced" image dataset.

At process block 312, the imaging data is reconstructed into a sequence of volumes corresponding to the different states of contrast passage through the vascular structures being studied. Both the mask and fill dataset may be preprocessed and converted to line integral images, such as using software available from the manufacturer of the x-ray imaging system. Then, the corresponding images from the mask (non-contrast) and fill (contrast-enhanced) 3D acquisitions can be subtracted to remove anatomical structures in the background and extract the contrast-enhanced areas of the vasculature.

The reconstruction step can be achieved with a variety of algorithms. For example, an iterative reconstruction process may be used along with retrospective gating. The projections are grouped according to when they were acquired within the cardiac/contrast injection cycle, and a 3D volume is reconstructed for each group. Since the number of projection angles per group is often relatively low (e.g. 6-12 projections spread out over the rotation; an amount equal to the number of injection cycles during imaging), there is potential for streaking artifacts in the reconstruction. This can be addressed with an iterative reconstruction algorithm where information from all projections is used to regularize the solution for each image volume.

While a variety of techniques for retrospectively-gated, iterative reconstruction following slow rotational acquisition may be used, the focus of the reconstructed images does not represent the boundaries of a periodically moving organ, such as lungs, or heart. Instead, in the case of imaging flow dynamics within a vascular structure, such as an aneurysm, the "object" is the temporally-evolving state of a compact contrast bolus that has been introduced to a vascular structure in order to study the internal patterns of blood flow. This substantially changes the concept of the reconstruction and can only be achieved using a properly configured power injector, such as described above with respect to FIG. 2, and an injection/acquisition protocol that is coordinated, such as described above, to create the necessary conditions for repeatedly creating an "object" that is really the dynamically flowing fluid within a void, and imaging the state of the "object" from different angles, thus enabling flow-resolved 3D imaging of internal flow patterns. In one non-limiting example, the image reconstruction at process 312 can be implemented as a multi-step process, such as will be described with respect to FIG. 3B.

In addition to being able to image an "object" that is really the dynamically flowing fluid within a void such as an aneurysm, the data acquired according to the above-described process can be used to provide a conventional 3D image of the vasculature without temporal resolution. That is, from the signal scan performed at process block 310, conventional 3D images of the vessels without temporal resolution or flow dynamics can also be delivered by applying performing a non-gated reconstruction technique at process block 312. In any case, at process block 314, a series of images can be provided that at least includes a time-resolved 3D volume showing flow dynamics that reflect the "object" being imaged, as described above.

Figure 3B:
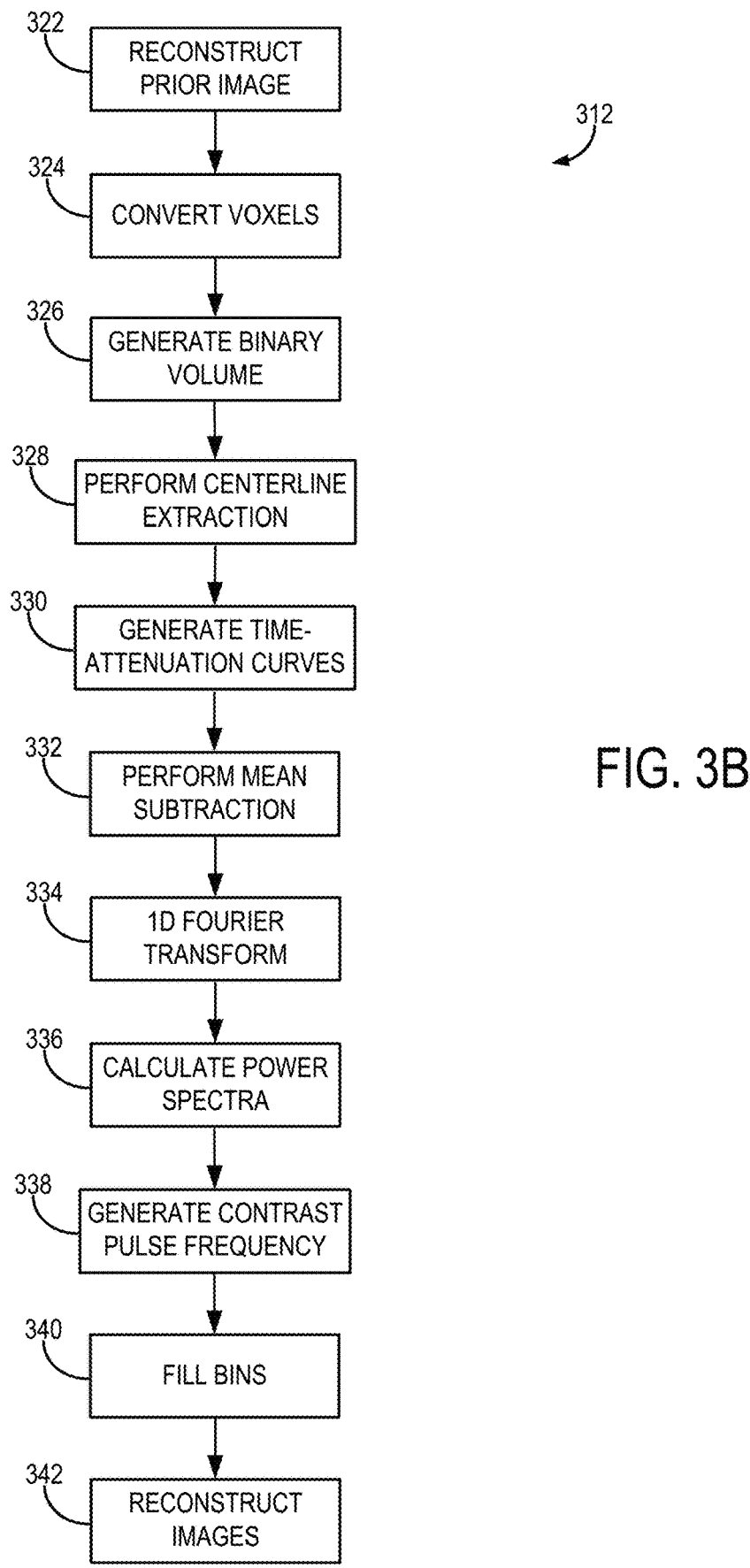
FIG. 3B is a flow chart setting forth some examples of steps in a reconstruction process in accordance with the present disclosure.

Referring now to FIG. 3B, one non-limiting example of an implementation of the reconstruction process block 312 of FIG. 3A is illustrated. Beginning at process block 322, a prior image of the 3D vasculature can be reconstructed using the commercial filtered backprojection (FBP) reconstruction algorithm. The reconstruction can be performed using the subtracted images from all projection angles. At process block 324, the voxel values can be subsequently converted from Hounsfield units to attenuation values and, at process block 326, a global threshold can be applied to generate a binary volume of the vasculature.

Then, a separate reconstruction is performed for each individual injection phase. In general, at 328, projection images can be partitioned into non-distinct bins corresponding to different phases. The partitioning can be automatically performed by a computer system applying a topology preserving thinning algorithm to the binary volume and extracting the centerlines of the vasculature. The points along the centerline of the input branch can be projected into each 2D projection and the corresponding gray values can be interpolated in the line integral images.

At process block 330, time attenuation curves can be generated along the centerline and a mean subtraction performed at process block 332. A process 334, a 1D Fourier transform can be then applied to the mean-subtracted time-attenuation curves for each centerline point and, at process block 336, the power spectrum can be calculated. At process block 338, the spectra can be average over all centerline points to identify the peak frequency, which can serve as "injection pulse frequency." Notably, the theoretical injection pulse frequency of the injector can differ from the measured "contrast pulse frequency," such as due to inaccuracies (or unknowns) in the timing of the image acquisition, frequency shifts caused by the vascular system, or other effects, such as if the injector is unable to achieve the exact waveform due to pressure limitations. Thus, identifying the peak frequency to serve as the "injection pulse frequency" overcomes these variables. However, in situations where such variables are not present, this step can be skipped and the "contrast pulse frequency" can be used. In one non-limiting example, a period length of $l_p=27.6$ projection images was measured, yielding a frequency=0.92 Hz. Each bin i is then filled at process block 340 with projection indices $b_i=\{x=i+\lambda \cdot l_p\}|\lambda=\{1,2,\ldots,\lceil n/l_p \rceil\}\}$. To increase the number of projections for each reconstruction, the adjacent projection images for each index in $b_i$ can be added to each bin.

At process block 342, each phase bin can be reconstructed separately using a binary volume constrained reconstruction technique. The particular reconstruction technique can be selected from a variety of reconstruction techniques. In one non-limiting example, the reconstruction algorithm can be the prior image constrained compressed sensing (PICCS) reconstruction process that can be performed using the prior image reconstructed at process block 322.

In one configuration, the iterative reconstruction algorithm can be modified to (1) allow changes only within the vascular lumen and (2) avoid early stopping due to local minima. To achieve (1), all voxels outside the binary volume can be set to 0 and not updated during each iteration of the reconstruction. Additionally, the iterative optimization strategy can be modified to avoid local minima, motivated by the fact that the prior reconstruction represents an average result using all projection images and might be close to a local minimum. At the beginning and after a predetermined number of iterations, such as every $30^{th}$ iteration, or when the average gradient size is smaller than a predefined value, a soft thresholding step can be performed by subtracting a global threshold from all voxel values in the reconstructions. Values smaller than zero can be set to zero. In one non-limiting example, the initial threshold values was 0.1/cm and is decreased by 0.02/cm with every soft thresholding step. This approach introduces additional energy into the optimization process and can avoid early stopping due to local minima.

The systems and methods provided herein overcome the drawbacks of prior systems for attempting to image vascular flow. For example, conventional 2D projection x-ray imaging, such as 2D-DSA, of injected contrast agent can be performed to visualize the flow of blood, but the 2D image does not provide 3D volumes. Thus, the clinician is not provided with a complete picture of the complex 3D flow patterns that exist inside large vascular structures, such as an aneurysm sac.

As another example, conventional 3D angiography with a C-arm system, such as 3D-DSA delineates the 3D geometry of vascular structures, but it contains no temporal information for the analysis of flow patterns. As such, 4D-DSA was developed that provides time-resolved imaging of contrast agent flow through a 3D vascular tree. However, 4D-DSA does not portray internal flow dynamics or fails when imaging many structures, such as non-tubular vascular structures. This is because 4D-DSA creates each "time frame" by back-projecting a single x-ray projection through a static 3D reconstruction of vascular structures. With this approach, there is no spatial resolution along the source-detector axis (the axis orientation for the given time-frame). Furthermore, the 4D-DSA process averages information between discrete vascular structures that overlap in the single 2D projection when they are used to reconstruct a time frame. Due to these limitations, flow analysis of 4D-DSA is generally limited to the analysis of blood flow propagation along tubular vessel structures, and reliable evaluations require corrections for overlap artifacts. Thus, all of these x-ray-based techniques fail when attempting to analyze flow patterns in a complex or non-tubular 3D structure, such as an aneurysm sac.

4D-Flow MRI can provide a detailed image of 3D blood flow patterns, and this modality could be regarded as the clinical reference standard. However, 4D-Flow MRI is not compatible with an interventional clinical environment that requires full patient access, rapid imaging, and/or a variety of catheter devices, which may contain metal. As such, it does not yield information that could be used in intra-procedural decision making, such as to determine if a device deployment was effective and the treatment endpoint has been achieved.

4D ultrasound is compatible with the interventional imaging environment; however, 4D ultrasound has very limited spatial resolution, particularly for deep structures. For example, for vascular structures in the head, transcranial ultrasound image quality is generally too poor to be a key clinical tool.

Computational fluid dynamics (CFD) simulation has been used in the research setting to analyze flow patterns. However, this is not practical in the clinical interventional setting because it requires lengthy computations, and the accuracy is sensitive to boundary conditions which may be unknown or poorly characterized clinically.

4D computed tomography (CT) using a diagnostic scanner and retrospectively gated reconstruction is missing several key elements necessary to address the clinical need. First, diagnostic scanners utilize closed bores and a closed-bore CT scanner is generally incompatible with an interventional workflow requiring arterial access, high spatial resolution fluoroscopic imaging of endovascular devices, and unrestricted patient access. Second, conventional CT injection protocols are intravenous and generally use one or more large boluses. The large boluses rely upon wash-in and wash-out dynamics to acquire flow information, which is insufficiently precise when imaging large vascular structures, such as an aneurysm sac.

Therefore, the present disclosure provides systems and methods not contemplated by the prior art. The systems and methods provided herein uses a specialized power injector to implement a particularly-programmed, timed sequence of compact contrast bolus injections. Traditional power injectors do not provide this capability. Furthermore, a particular acquisition and reconstruction process is provided that, when coupled with the injection protocol, yields images not available using traditional hardware or software.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for acquiring images of three-dimensional flow within an interior volume of a subject, the system comprising:
   a power injector programmable to deliver a contrast agent as a series of boluses using a known at least one of period, flow rate, or duration and with a bolus rate of at least one or more boluses per cardiac cycle of the subject;
   an x-ray imaging system configured to acquire a reference dataset of the subject before the contrast agent is delivered to the subject and to acquire an imaging dataset as the series of boluses are delivered to the subject, wherein multiple images are acquired of the subject per bolus; and
   a computer system configured to:
      receive the reference dataset and the imaging dataset from the x-ray imaging system; and
      reconstruct the reference dataset and the imaging dataset using the bolus rate in a reconstruction process that removes the subject from the images to generate time-resolved volumetric images of the contrast agent moving within a volume of the subject without the subject.

2. The system of claim 1 wherein the period is equal to an integer multiple of cardiac cycle of the subject.

3. The system of claim 1 wherein the computer is further programmed to perform an iterative reconstruction process with retrospective gating based on at least one of the cardiac cycle or the period of the series boluses to reconstruct the imaging dataset.

4. The system of claim 3 wherein the iterative reconstruction process uses the contrast agent as an object of the iterative reconstruction process.

5. The system of claim 1 wherein the computer system is further programmed to generate a binary volume of vasculature through which the series of boluses flow.

6. The system of claim 1 wherein the computer system is further programmed to perform a separate reconstruction for each individual injection phase in the series of boluses.

7. The system of claim 1 wherein the x-ray imaging system is configured to rotate about the subject at a rotation time selected to acquire multiple images per injection period.

8. The system of claim 1 wherein power injector is configured to prospectively gate the series of boluses relative to a physiological cycle of the subject.

9. The system of claim 1 wherein the power injector is configured to vary one of a volume or a concentration of contrast agent delivered to the subject to deliver series of boluses.

10. The system of claim 1 wherein the power injector is configured to deliver the one or more boluses using a predetermined amount or concentration of contrast agent.

11. The system of claim 10 wherein the power injector is further configured to deliver a second predetermined amount or concentration of contrast agent that is less than the predetermined amount or concentration of contrast agent between the one or more boluses.

12. A system for acquiring images of three-dimensional flow within an interior volume of a subject, the system comprising:
   a power injector programmable to deliver a contrast agent as a series of boluses using a known at least one of period, flow rate, or duration and with a rate of at least one or more boluses per cardiac cycle of the subject;
   an x-ray imaging system configured to acquire a reference dataset of the subject before the contrast agent is delivered to the subject and to acquire an imaging dataset as the series of boluses are delivered to the subject, wherein multiple images are acquired of the subject per bolus; and
   a computer system configured to:
      receive the reference dataset and the imaging dataset from the x-ray imaging system;
      reconstruct the reference dataset and the imaging dataset using a reconstruction process that removes the subject from the images to generate time-resolved volumetric images of the contrast agent moving within a volume of the subject without the subject; and
   wherein the computer system is further programmed to determine time attenuation curves through the subject and determine a power spectrum.

13. The system of claim 12 wherein the computer system is further programmed to determine an injection pulse frequency using the power spectrum.

14. The system of claim 13 wherein the computer system is further programmed to use the injection pulse frequency to divide the imaging dataset into phase bins and separately reconstruct portions of the imaging dataset assigned to each phase bin.

15. A system for acquiring images of three-dimensional flow within an interior volume of a subject, the system comprising:
   a power injector programmable to deliver a contrast agent as a series of boluses using a known at least one of period, flow rate, or duration and with a rate of at least one or more boluses per cardiac cycle of the subject;
   an x-ray imaging system configured to acquire a reference dataset of the subject before the contrast agent is delivered to the subject and to acquire an imaging dataset as the series of boluses are delivered to the subject, wherein multiple images are acquired of the subject per bolus; and a computer system configured to:
receive the reference dataset and the imaging dataset from the x-ray imaging system;
reconstruct the reference dataset and the imaging dataset using a reconstruction process that removes the subject from the images to generate time-resolved volumetric images of the contrast agent moving within a volume of the subject without the subject; and
wherein the computer system is further programmed to partition the imaging dataset into non-distinct bins corresponding to injection phases.

16. A system for acquiring images of three-dimensional flow within an interior volume of a subject, the system comprising:
a power injector programmable to deliver a contrast agent as a series of boluses using a known at least one of period, flow rate, or duration and with a rate of at least one or more boluses per cardiac cycle of the subject;
an x-ray imaging system configured to acquire a reference dataset of the subject before the contrast agent is delivered to the subject and to acquire an imaging dataset as the series of boluses are delivered to the subject, wherein multiple images are acquired of the subject per bolus; and
a computer system configured to:
receive the reference dataset and the imaging dataset from the x-ray imaging system;
reconstruct the reference dataset and the imaging dataset using a reconstruction process that removes the subject from the images to generate time-resolved volumetric images of the contrast agent moving within a volume of the subject without the subject; and
wherein the computer system is further programmed to perform an iterative reconstruction algorithm that allows changes only within a flow path through vascular structures, including non-tubular volumes, and controls against local minima.

17. A system for acquiring images of three-dimensional flow within an interior volume of a subject, the system comprising:
a power injector programmable to deliver a contrast agent as a series of boluses using a known at least one of period, flow rate, or duration and with a rate of at least one or more boluses per cardiac cycle of the subject;
an x-ray imaging system configured to acquire a reference dataset of the subject before the contrast agent is delivered to the subject and to acquire an imaging dataset as the series of boluses are delivered to the subject, wherein multiple images are acquired of the subject per bolus; and
a computer system configured to:
receive the reference dataset and the imaging dataset from the x-ray imaging system;
reconstruct the reference dataset and the imaging dataset using a reconstruction process that removes the subject from the images to generate time-resolved volumetric images of the contrast agent moving within a volume of the subject without the subject; and wherein at least one of:
the power injector is configured to deliver between 5 and 20 boluses per injection period;
the x-ray imaging system is configured to use an acquisition rate of between 15 and 30 frame/second for each injection period with a rotation time of between 6 and 12 second; or
the power injector is configured to deliver each contrast bolus with a volume of approximately 4 mL.

18. A method for creating an image of flow within a subject, the method including steps comprising:
a) programming a power injector to deliver a contrast agent to the subject as a series of boluses to deliver the boluses at a bolus rate of one or more boluses per cardiac cycle using a known at least one of period, flow rate, or duration of the series of boluses;
b) acquiring a reference image dataset of the subject in the absence of the contrast agent;
c) acquiring a medical image dataset of the subject during operation of the power injector as the one or more boluses per cardiac cycle are delivered to the subject, wherein multiple images are acquired per bolus;
d) reconstructing the medical image dataset using the bolus rate and the reference image dataset to create a series three-dimensional (3D) volumes of the contrast agent as the contrast agent dynamically moves with the known at least one of period, flow rate, or duration through the subject.

19. The method of claim 18 wherein the period is equal to an integer multiple of cardiac cycle.

20. The method of claim 18 wherein reconstructing includes performing an iterative reconstruction process with retrospective gating based on at least one of the cardiac cycle or the period of the series boluses.

21. The method of claim 20 wherein the iterative reconstruction process is configured to use the contrast agent as an object of the iterative reconstruction process.

22. The method of claim 20 wherein the iterative reconstruction process includes a prior-image constrained compressed sensing (PICCS) reconstruction process.

23. The method of claim 18 wherein reconstructing includes subtracting images reconstructed from the medical image dataset and images reconstructed from the reference image dataset.

24. The method of claim 18 wherein reconstructing includes generating a binary volume of vasculature through which the series of boluses flow.

25. The method of claim 18 wherein reconstructing further includes partitioning images into non-distinct bins corresponding to injection phases.

26. The method of claim 18 wherein reconstructing includes performing a separate reconstruction for each individual injection phase in the series of boluses.

27. The method of claim 18 wherein acquiring the medical image dataset includes rotating an x-ray imaging system about the subject to acquire x-ray images using a rotation time selected to acquire multiple images per injection period.

28. The method of claim 18 wherein medical image dataset is acquired from a non-tubular volume in the subject.

29. The method of claim 18 further comprising prospectively gate the series of boluses relative to a physiological cycle of the subject.

30. The method of claim 18 wherein physiological cycle is a cardiac cycle of the subject.

31. The method of claim 18 further comprising to vary one of a volume or a concentration of contrast agent delivered to the subject to deliver series of boluses.

32. A method for creating an image of flow within a subject, the method including steps comprising:
   a) programming a power injector to deliver a contrast agent to the subject as a series of boluses to deliver one or more boluses per cardiac cycle using a known at least one of period, flow rate, or duration of the series of boluses;
   b) acquiring a reference image dataset of the subject in the absence of the contrast agent;
   c) acquiring a medical image dataset of the subject during operation of the power injector as the one or more boluses per cardiac cycle are delivered to the subject, wherein multiple images are acquired per bolus;
   d) reconstructing the medical image dataset and the reference image dataset to create a series three-dimensional (3D) volumes of the contrast agent as the contrast agent dynamically moves with the known at least one of period, flow rate, or duration through the subject; and
   wherein reconstructing includes determining time attenuation curves through the subject and determining a power spectrum.

33. The method of claim 32 further comprising determining an injection pulse frequency using the power spectrum.

34. The method of claim 33 wherein reconstructing includes using the injection pulse frequency to divide the medical image dataset into phase bins and separately reconstructing portions of the medical image dataset assigned to each phase bin.

35. A method for creating an image of flow within a subject, the method including steps comprising:
   a) programming a power injector to deliver a contrast agent to the subject as a series of boluses to deliver one or more boluses per cardiac cycle using a known at least one of period, flow rate, or duration of the series of boluses;
   b) acquiring a reference image dataset of the subject in the absence of the contrast agent;
   c) acquiring a medical image dataset of the subject during operation of the power injector as the one or more boluses per cardiac cycle are delivered to the subject, wherein multiple images are acquired per bolus;
   d) reconstructing the medical image dataset and the reference image dataset to create a series three-dimensional (3D) volumes of the contrast agent as the contrast agent dynamically moves with the known at least one of period, flow rate, or duration through the subject; and
   wherein reconstructing includes performing an iterative reconstruction algorithm that allows changes only within a flow path through vascular structures, including non-tubular volumes, and controls against local minima.

36. A method for creating an image of flow within a subject, the method including steps comprising:
   a) programming a power injector to deliver a contrast agent to the subject as a series of boluses to deliver one or more boluses per cardiac cycle using a known at least one of period, flow rate, or duration of the series of boluses;
   b) acquiring a reference image dataset of the subject in the absence of the contrast agent;
   c) acquiring a medical image dataset of the subject during operation of the power injector as the one or more boluses per cardiac cycle are delivered to the subject, wherein multiple images are acquired per bolus;
   d) reconstructing the medical image dataset and the reference image dataset to create a series three-dimensional (3D) volumes of the contrast agent as the contrast agent dynamically moves with the known at least one of period, flow rate, or duration through the subject; and
   wherein the series of boluses form at least one of a square wave or sinusoidal wave.

37. A method for creating an image of flow within a subject, the method including steps comprising:
   a) programming a power injector to deliver a contrast agent to the subject as a series of boluses to deliver one or more boluses per cardiac cycle using a known at least one of period, flow rate, or duration of the series of boluses;
   b) acquiring a reference image dataset of the subject in the absence of the contrast agent;
   c) acquiring a medical image dataset of the subject during operation of the power injector as the one or more boluses per cardiac cycle are delivered to the subject, wherein multiple images are acquired per bolus;
   d) reconstructing the medical image dataset and the reference image dataset to create a series three-dimensional (3D) volumes of the contrast agent as the contrast agent dynamically moves with the known at least one of period, flow rate, or duration through the subject; and
   wherein the one or more boluses are separated by a continued delivery of contrast at a lower injection rate than delivered during the one or more boluses.

* * * * *